United States Patent
Martineau et al.

(10) Patent No.: US 9,440,266 B2
(45) Date of Patent: Sep. 13, 2016

(54) WASHER / DISINFECTOR HAVING A WATER INLET DIFFUSER

(71) Applicant: STERIS INC., Temecula, CA (US)

(72) Inventors: Louis Martineau, St-Nicolas (CA); Maxime Robert, L'Ancienne-Lorette (CA)

(73) Assignee: STERIS INC., Temecula, CA (US)

( * ) Notice: Subject to any disclaimer, the term of this patent is extended or adjusted under 35 U.S.C. 154(b) by 0 days.

(21) Appl. No.: 13/787,899

(22) Filed: Mar. 7, 2013

(65) Prior Publication Data

US 2014/0150827 A1    Jun. 5, 2014

Related U.S. Application Data (60) Provisional application No. 61/731,591, filed on Nov. 30, 2012.

(51) Int. Cl.
| | |
|---|---|
| *B08B 3/02* | (2006.01) |
| *A47L 15/16* | (2006.01) |
| *A61L 2/24* | (2006.01) |
| *B08B 3/10* | (2006.01) |
| *A61L 9/14* | (2006.01) |
| *A47L 15/22* | (2006.01) |

(52) U.S. Cl.
CPC .............. *B08B 3/10* (2013.01); *A61B 90/70* (2016.02); *A61L 2/24* (2013.01); *A61L 9/14* (2013.01); *B08B 3/02* (2013.01); *A47L 15/16* (2013.01); *A47L 15/22* (2013.01); *A61L 2202/14* (2013.01); *A61L 2202/17* (2013.01); *A61L 2202/24* (2013.01)

(58) Field of Classification Search
CPC ............... A47L 15/14; A47L 15/4208; A47L 15/4088; B08B 3/02; A61L 2/24; A61L 9/14; A61B 90/70
USPC ............... 134/172, 198, 105, 108, 199, 95.3
See application file for complete search history.

(56) References Cited

U.S. PATENT DOCUMENTS

| | | | |
|---|---|---|---|
| 2,987,260 A | * | 6/1961 | Sasnett ............... A47L 15/23 134/176 |
| 3,001,533 A | * | 9/1961 | Holdren ................ 134/166 R |

(Continued)

FOREIGN PATENT DOCUMENTS

| | | | | |
|---|---|---|---|---|
| FR | EP 0524102 A1 | * | 1/1993 | ............. A47L 15/23 |
| IT | EP 0766945 A2 | * | 4/1997 | ......... A47L 15/0057 |

(Continued)

OTHER PUBLICATIONS

Form PCT/ISA/210—Int'l Search Report (from corresponding Int'l Patent App. No. PCT/US2013/30309—1 page.

(Continued)

*Primary Examiner* — Joseph L Perrin
*Assistant Examiner* — Irina Graf
(74) *Attorney, Agent, or Firm* — Kusner & Jaffe; Michael A. Centanni (57) ABSTRACT

A washer having a plurality of water inlet diffusers, each diffuser connected to a water inlet line for directing the flow of fluid into the washing chamber. The water is directed, i.e., sprayed against the surfaces of the washing chamber to modify (adjust) the temperature of the washing chamber gradually prior to the start of a particular phase of a washing cycle.

17 Claims, 3 Drawing Sheets

(56) References Cited

U.S. PATENT DOCUMENTS

| | | | | |
|---|---|---|---|---|
| 3,774,626 | A * | 11/1973 | Schweitzer | 134/179 |
| 3,854,998 | A * | 12/1974 | Jacobs | 134/191 |
| 4,895,178 | A | 1/1990 | McHugh | 134/167 C |
| 5,131,419 | A * | 7/1992 | Roberts | A47L 15/0078 |
| | | | | 134/113 |
| 5,759,289 | A * | 6/1998 | Caron et al. | 134/34 |
| 5,816,273 | A | 10/1998 | Milocco et al. | 134/108 |
| 6,418,943 | B1 * | 7/2002 | Miller | A47L 15/4202 |
| | | | | 134/104.1 |
| 6,568,413 | B1 * | 5/2003 | Hurskainen | B08B 9/0936 |
| | | | | 134/166 R |
| 7,520,288 | B2 | 4/2009 | Rhodes | 134/200 |
| 7,985,298 | B2 | 7/2011 | Purtilo et al. | 134/25.2 |
| 8,002,903 | B1 | 8/2011 | Tarr | 134/57 D |
| 8,221,554 | B2 | 7/2012 | Thiyagarajan | 134/10 |
| 2008/0289654 | A1 * | 11/2008 | Kim et al. | 134/18 |
| 2009/0025758 | A1 * | 1/2009 | Watson | A47L 15/16 |
| | | | | 134/70 |
| 2010/0024240 | A1 | 2/2010 | Robert et al. | 34/218 |
| 2011/0017234 | A1 * | 1/2011 | Lehmann | 134/10 |
| 2011/0139181 | A1 * | 6/2011 | Lee | A47L 15/0015 |
| | | | | 134/18 |
| 2014/0069473 | A1 * | 3/2014 | Baldwin | A47L 15/4246 |
| | | | | 134/56 D |

FOREIGN PATENT DOCUMENTS

| | | |
|---|---|---|
| WO | WO 2007/127654 A2 | 11/2007 |
| WO | WO 2008/136341 A1 | 11/2008 |

OTHER PUBLICATIONS

Office Action issued in corresponding Canadian Patent Application No. 2,892,307.

Extended European Search Report issued in corresponding European Patent Application No. 13858664.9-1659 dated Jun. 27, 2016.

* cited by examiner

WASHER / DISINFECTOR HAVING A WATER INLET DIFFUSER

FIELD OF THE INVENTION

The present invention relates generally to the cleaning and decontaminating arts, and more particularly to washers and disinfectors for washing and disinfecting instruments and equipment, such as surgical, medical, dental, veterinary and mortuary instruments and equipment that contain or potentially contain, biological contaminants.

BACKGROUND OF THE INVENTION

Medical washers are conventionally known and are used to clean instruments and equipment that are exposed to biological contaminants. Such washers typically clean the instruments and equipment by directing jets or streams of fluid at the instrument and/or equipment from spray heads or nozzles located within the washer. A typical cleaning operation may include a preliminary rinse cycle, a pre-wash cycle, and a wash cycle (where the instruments and equipment are exposed to one or more chemical cleaning solutions), a rinse cycle and a thermal rinse cycle.

During these various phases of a washing cycle, fluids are introduced into the washing chamber by pumps to effect the washing or rinsing of the articles to be cleaned. The fluids used within the washing chamber during the different cycles often have significantly different temperatures. For example, during a pre-wash phase, cold water from a facilities' cold water lines (i.e., tap water) is typically used. The wash phase typically uses water (with added detergents and chemicals) from the facilities' water lines, the water being heated within the washing chamber to about 150° F. (The heating of fluids within the washer typically occurs in a sump located at the bottom of the washing chamber where the washing fluids are collected). The rinse phase typically uses hot water from the facilities' hot water line. A thermal rinse typically uses pure, high-quality water that is heated within the washer to about 190° F.

The use of hot and cold fluids within the washing chamber during the different phases of the washing cycle, as well as the starting and stopping of pumps, can produce significant fluctuation in pressure within the washing chamber between the different phases of the washing cycle. More specifically, changes in temperature of the fluids used during the different phases of a washing cycle and the starting and stopping of pumps can produce either an increased pressure in the washing chamber, as compared to the surrounding environment (i.e., a positive pressure), or a vacuum within the washing chamber as compared to the surrounding environment (i.e., a negative pressure). These occurrences are referred to as "thermal shock."

To reduce "thermal shock" during operation, washers/disinfectors known heretofore typically include a two-speed motor to pump washing and rinsing fluids through the washer/disinfector. The two-speed pump operates at a low speed during the initial start of a cycle phase to introduce the fluid into the washing chamber at a low rate to minimize the thermal shock created in the washing chamber during the start-up procedure.

The aforementioned types of washers/disinfectors having two-speed motors are typically used in large hospital and medical facilities. However, there is also a need for a less expensive, instrument washer for small clinics and one-day surgical centers. To help reduce the cost of a washer/disinfector for small clinics and one-day surgical centers, use of a one-speed pump is desirable.

The present invention provides a washer/disinfector having inlet diffusers to distribute fluids entering a washing chamber during operating phases to reduce the thermal shock that may occur during a washing cycle.

SUMMARY OF THE INVENTION

In accordance with a preferred embodiment of the present invention, there is provided a washer having a plurality of water inlet diffusers, each diffuser connected to a water inlet line for directing the flow of fluid into the washing chamber. The water is directed, i.e., sprayed against the surfaces of the washing chamber to modify (adjust) the temperature of the washing chamber gradually prior to the start of a particular phase of a washing cycle.

In accordance with another aspect of the present invention, there is provided a washing apparatus for washing medical devices. The washing apparatus has a washing chamber, a sump at the bottom of the washing chamber for collecting and holding fluids, a heating element in the sump for heating fluids in the sump, a sprayer for spraying the fluids on the medical devices to be cleaned, and a pump for pumping fluids in the sump to the sprayer. Two or more fluid inlet lines provide fluid to the washing chamber. Each of the fluid lines is connected to a fluid diffuser that is mounted to a wall defining the washing chamber. The diffuser is comprised of a tubular body portion having a domed portion at one end thereof. The domed portion has an inner chamber. The inner chamber communicates with the exterior of the domed portion through a plurality of apertures extending through the domed portion. The apertures are directed toward the wall defining the washing chamber, wherein fluid entering the washing chamber through the fluid inlet lines is directed toward the wall.

In accordance with another aspect of the present invention, there is provided a method of washing medical devices in a washing apparatus, the washing apparatus having a washing chamber, a sump at the bottom of the washing chamber for collecting and holding fluids, a sprayer for spraying the fluids on the medical devices to be cleaned, and a pump for pumping fluids in the sump to the sprayer. The method comprises the steps of:
 introducing water at a first temperature in the washing chamber through a first diffuser having a plurality of apertures directing the water toward a wall defining the washing chamber;
 collecting the water in the sump;
 initiating the pump to start a first phase of a washing cycle;
 deactivating the pump;
 draining the water from the washing chamber;
 introducing water at a second temperature in the washing chamber through a second diffuser having a plurality of apertures directing the water toward a wall defining the washing chamber;
 collecting the water in the sump; and
 initiating the pump to start a second phase of a washing cycle.

In accordance with another aspect of the present invention, a plurality of water inlet diffusers are mounted to a wall of the washing chamber and each diffuser is connected a water inlet on an exterior side of the wall of the washing chamber.

An advantage of the present invention is a washer/disinfector for washing medical instruments.

Another advantage of the present invention is a water inlet diffuser for use on a washer/disinfector as described above.

A still further advantage of the present invention is a water inlet diffuser as described above that can be easily mounted to a wall panel defining a washing chamber.

A still further advantage of the present invention is a water inlet diffuser as described above that directs the flow of incoming water against a wall or walls of the washer to gradually change the temperature of the wall(s) of the washing chamber during phases of a washing cycle.

Another advantage of the present invention is a water inlet diffuser as described above that is formed of silicon.

Another advantage of the present invention is a water inlet diffuser as described above that is easily mounted to the wall panel of the wall chamber.

A still further advantage of the present invention is a water inlet diffuser as described above that forms a seal with the wall chamber forming the washing chamber.

These and other advantages will become apparent from the following description of a preferred embodiment taken together with the accompanying drawings and the appended claims.

BRIEF DESCRIPTION OF THE DRAWINGS

The present invention may take physical form in certain parts and arrangement of parts, preferred embodiments of which will be described in detail in the specification and illustrated in the accompanying drawings which form a part hereof, and wherein.

DETAILED DESCRIPTION OF PREFERRED EMBODIMENTS

Figure 1:
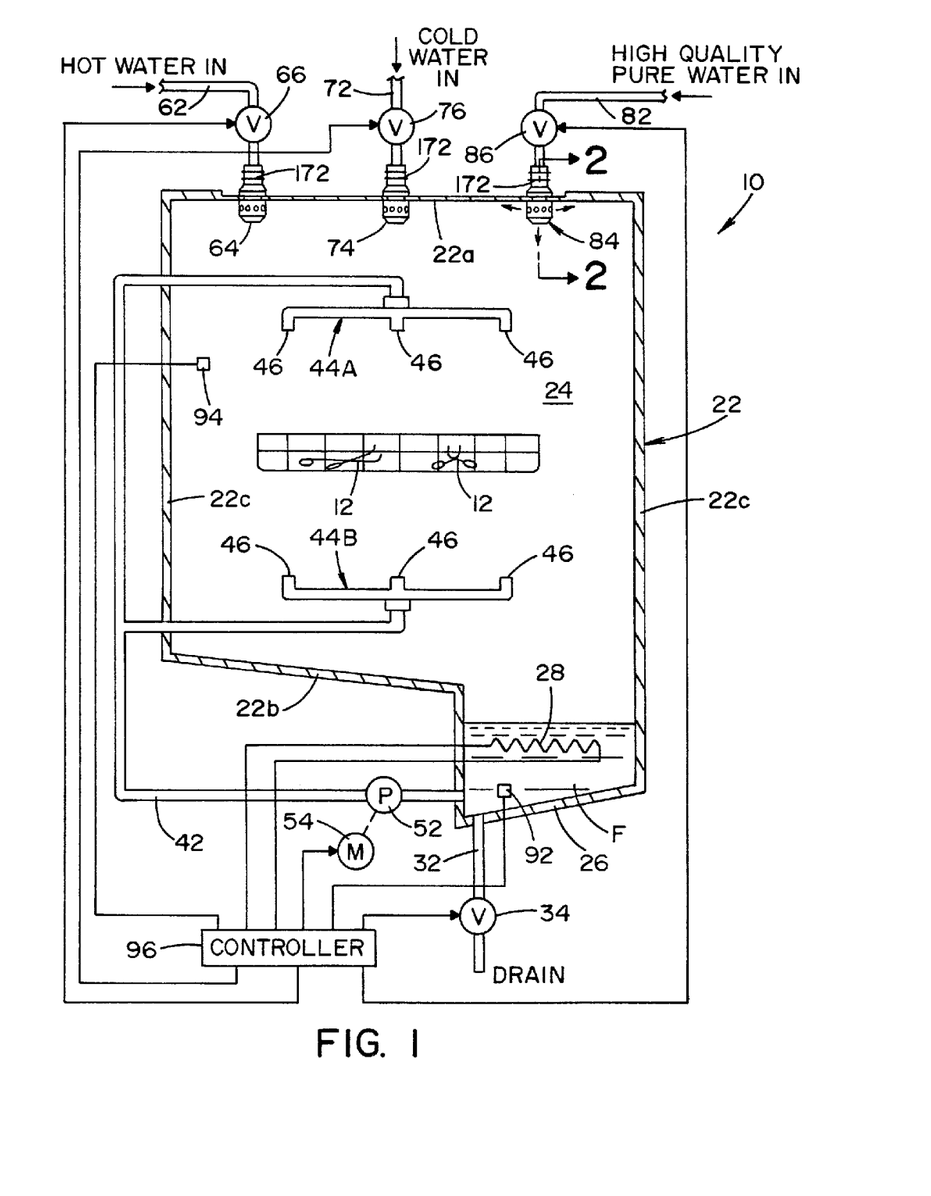
FIG. 1 is a schematic view of a washer illustrating one embodiment of the present invention.

Referring now to the drawings wherein the showings are for the purpose of illustrating preferred embodiments of the invention only, and not for the purpose of limiting same, FIG. 1 schematically illustrates a medical washer 10 for washing medical instruments and equipment 12, such as, by way of example and not limitation, surgical, medical, dental, veterinary and mortuary instruments and equipment.

Washer 10 includes a housing 22 having a top wall 22a, a bottom wall 22b and side walls 22c. Housing 22 defines a washing chamber 24. Housing 22 is formed to include a sloped sump 26 that is disposed at the bottom of washing chamber 24. As will be described in greater detail below, sump 26 is provided to receive washing fluids or rinsing fluids, designated "F" in the drawing that are used in washing chamber 24. A heating element 28 is provided in sump 26 to heat washing fluids or rinsing fluids F. A drain 32 is formed in the bottom of sump 26. A valve 34 is provided within drain 32 to control the flow of washing fluids or rinsing fluids F therethrough. A circulation conduit 42 communicates with sump 26 and connects sump 26 to first and second sprayer arms 44A, 44B having spray heads 46 therein. First sprayer arm 44A is disposed in the upper portion of washing chamber 24 with spray heads 46 directed downward. Second sprayer arm 44B is disposed in the lower portion of washing chamber 24 with spray heads 46 directed upward. In this respect, spray heads 46 direct washing fluids or rinsing fluids F toward the center of washing chamber 24 and medical instruments 12, as illustrated in FIG. 1. A pump 52 is provided within circulation conduit 42 to pump fluids F from sump 26 to spray heads 46. Pump 52 is driven by a motor 54, as schematically illustrated in FIG. 1.

A first water supply line 62 has a first end that is connectable to a source of hot water, as illustrated in FIG. 1, and a second end connected to a water inlet diffuser 64. A valve 66 within water supply line 62 controls flow of the water from the hot water supply source (not shown) to diffuser 64. A second water supply line 72 has a first end that is connectable to a source of cold water, as illustrated in FIG. 1, and a second end connected to a water inlet diffuser 74. A valve 76 within water supply line 72 controls flow of the water from the cold water supply source (not shown) to diffuser 74. A third water supply line 82 has a first end that is connectable to a source of high-quality, pure water, as illustrated in FIG. 1, and a second end connected to a water inlet diffuser 84. A valve 86 within water supply line 82 controls flow of the water from the high-quality, pure water supply source (not shown) to diffuser 84.

A temperature sensor 92 is disposed within sump 26 and a humidity sensor 94 is disposed within washing chamber 24. Sensors 92, 94 are operable to provide electrical signals indicative of the temperature of fluid F in sump 26 and the humidity in washing chamber 24, respectively, to a controller 96. Controller 96 is programmed to control the operation of washer 10. As schematically illustrated in FIG. 1, controller 96 is operatively connected to sensors 92, 94, to receive signals therefrom, and to motor 54 and valves 34, 66, 76 and 86 to control the operation thereof.

Referring now to FIGS. 2-8, diffuser 84, according to another aspect of the present invention, is shown. Since diffusers 64, 74 and 84 shown in FIG. 1 are identical, only diffuser 84 shall be described in detail, it being understood that such description also applies to diffusers 64 and 74.

Diffuser 84 is comprised of a tubular body portion 112 having an enlarged, domed portion 114 formed at one end thereof. Body portion 112 is generally cylindrical in shape and has a cylindrical outer surface 112a. A cylindrical bore 116, best seen in FIGS. 3 and 6, extends through body portion 112 along an axis "A." In the embodiment shown, domed portion 114 of diffuser 84 is cylindrical in shape and defines an inner cavity 118 that communicates with bore 116 that extends through body portion 112. Domed portion 114 of diffuser 84 has an outer cylindrical surface 114a having a diameter larger than outer cylindrical surface 112a of body portion 112. Domed portion 114 has an end wall 122 having a flat, outer end surface 122a that is generally perpendicular to axis "A" of bore 116 in body portion 112. End wall 122 has an inner surface 122b that is slightly concave. A chamfered surface 124 connects outer surface 114a of domed portion 114 to flat end surface 122a. A conical, sloping surface 126 connects outer surface 114a of domed portion 114 to outer surface 112a of body portion 112.

Diffuser 84 is generally symmetrical about axis "A," and is preferably formed as an integral component from a resilient, flexible elastomeric material, such as, by way of example and not limitation, silicone or rubber. As best see in FIG. 2, diffuser 84 is dimensioned to be mounted in a circular hole in a generally flat portion of top wall 22a of washer housing 22. In this respect, an annular slot 132 is formed in outer surface 114a of domed portion 114 of diffuser 84. Annular slot 132 in diffuser 84 is dimensioned to receive the inner edge of top wall 22a that defines the hole. Annular slot 132 is disposed on domed portion 114 such that a major part of domed portion 114 is disposed within washing chamber 24.

Figure 2:
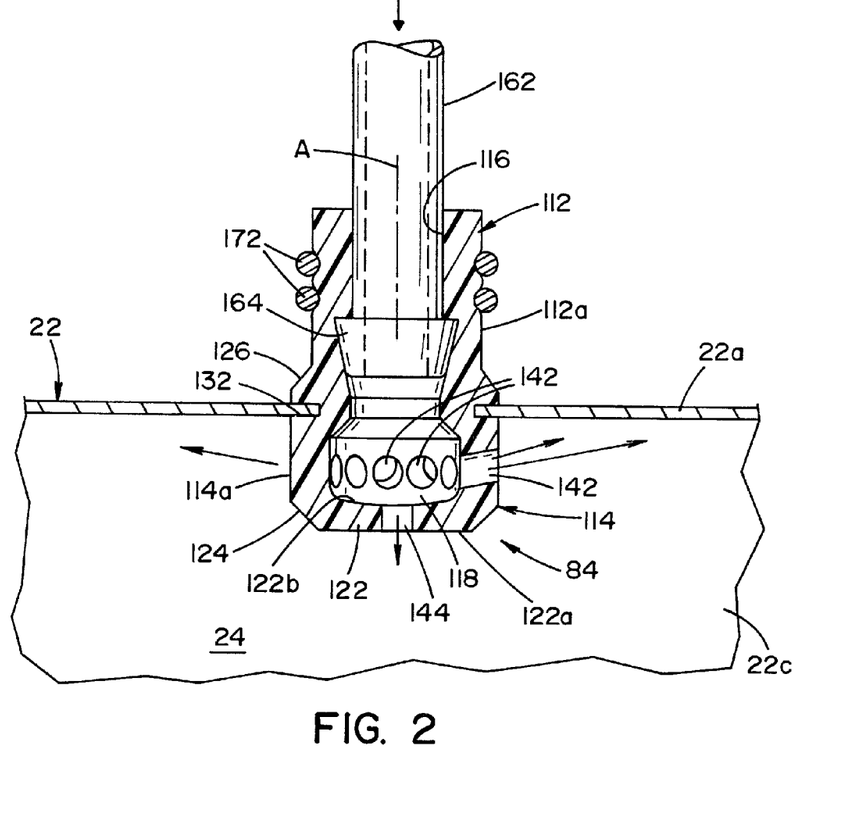
FIG. 2 is an enlarged, sectional view taken along lines 2-2 of FIG. 1 showing a water inlet diffuser mounted to the upper wall of a washing chamber.
Figure 3:
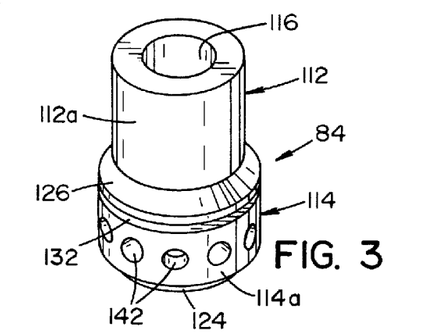
FIG. 3 is a top, perspective view of the water inlet diffuser shown in FIG. 2.
Figure 4:
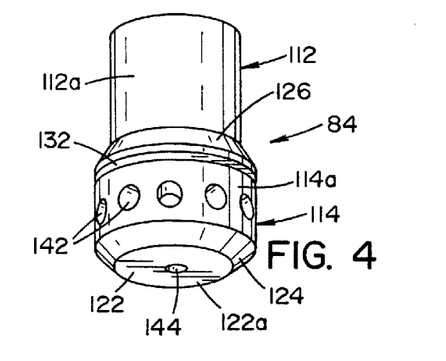
FIG. 4 is a bottom, perspective view of the water inlet diffuser.
Figure 5:
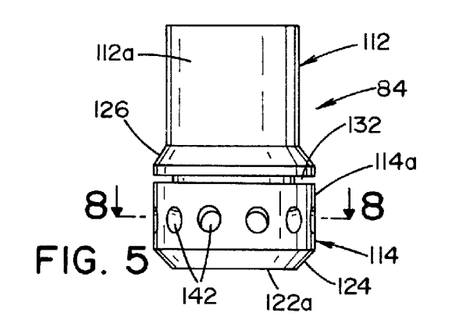
FIG. 5 is a side, elevational view of the water inlet diffuser.
Figure 6:
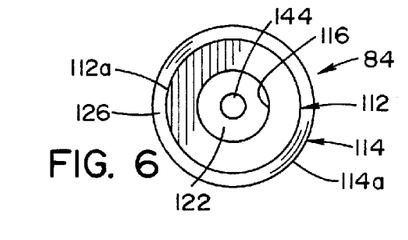
FIG. 6 is a top view of the water inlet diffuser.
Figure 7:
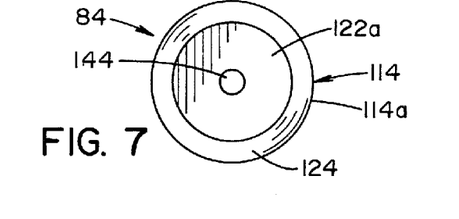
FIG. 7 is a bottom view of the water inlet diffuser.
Figure 8:
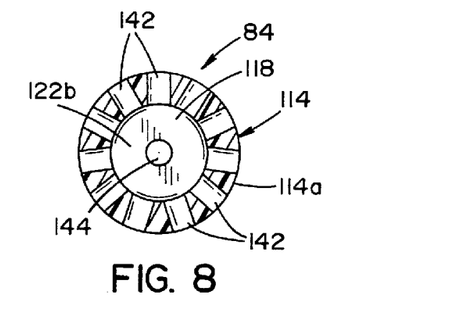
FIG. 8 is a sectional view taken along lines 8-8 of FIG. 5.

In the embodiment shown in FIG. 2, diffuser 84 is shown mounted to top wall 22a of washing chamber 24. As will be appreciated from a further reading of the present specification, a diffuser 64, 74, 84 may also be mounted to one or more of side walls 22c that form washing chamber 24.

A plurality of apertures 142 is formed in domed portion 114 of diffuser 84. Inner chamber 118 communicates with the exterior of diffuser 84 through apertures 142. At least one aperture 144 extends through end wall 122 of diffuser 84. Aperture 144 is preferably aligned with bore 116 extending through tubular portion 112 of diffuser 84. Apertures 142 extend through the side of domed portion 114 from inner chamber 118 to outer surface 114a of diffuser 84. In the embodiment shown in the drawings, apertures 142 have like dimensions and are equally spaced about axis "A" through diffuser 84. Apertures 142 are preferably angled slightly away from end wall 122 of diffuser 84. In other words, apertures 142 are oriented back toward top wall 22a to which diffuser 84 is attached. In the embodiment shown, apertures 142 are directed away from end wall 122 at an angle of about 10° (angular degrees) relative to a plane perpendicular to axis "A."

Aperture 144 through end wall 122 of diffuser 84 and apertures 142 through the side of domed portion 114 of diffuser 84 are dimensioned such that the total cross-sectional area of all the apertures is generally equal to or slightly less than the cross-sectional area of bore 116 through body portion 112 of diffuser 84.

Each diffuser 64, 74, 84 is dimensioned to be attached to a fluid inlet tube 162. Preferably, fluid inlet tube 162 has a barbed end 164 which is dimensioned to be inserted into bore 116 of body portion 112, as shown in FIG. 2. A conventional tube clamp 172, only partially shown in FIG. 2, is used to compress and secure tubular body portion 112 of diffuser 84 to the end of fluid inlet tube 162.

Referring now to the operation of washer 10, a preferred washing cycle includes a pre-wash phase, a wash phase, a rinse phase and a thermal rinse phase. At the beginning of the pre-wash phase, a pre-wash fluid is introduced into washing chamber 24. The pre-wash fluid is basically cold water from an external source, i.e., a cold water line from an institution's water system. The cold water typically is at a temperature below room temperature. The cold water is introduced in washing chamber 24 through inlet line 72 and diffuser 74. (A cleaning chemical may be added to the cold water). The incoming cold water is distributed into washing chamber 24 through diffuser 74. More specifically, the incoming cold water is distributed, i.e., diffused, by diffuser 74 such that the cold water is directed toward the inner surface of top wall 22a. Some of the cold water would typically flow down along side wall 22c that forms the sides of washing chamber 24. The cold water is ultimately collected into sump 26 at the bottom of washing chamber 24. Some of the water flowing through diffuser 74 would fall or splash onto spray arms 44A, 44B as well as onto medical instruments 12. In this way, the cold water flowing through diffuser 74 is more widely distributed to surfaces within washing chamber 24 and onto structural components of spray arms 44A, 44B, as well as onto instruments 12 to be washed.

In this respect, water entering washing chamber 24 in streams along surfaces of the washing chamber, is more likely to gradually heat or cool the surfaces within washing chamber 24, but not heat or cool the air within the washing chamber. As compared to a hot spray introduced into a cold washing chamber or a cold spray introduced into a warm washing chamber, the thermal energy transferred by a stream of fluid onto a surface is more gradual, as the heated or cooled surface then heats or cools the air within the washing chamber in more gradual fashion, as compared to the rapid transfer of thermal energy by droplets and mists of a fluid introduced into a region of space. When sufficient water is introduced into washing chamber 24, controller 96 closes valve 76. Controller 96 then starts motor 54 that causes pump 52 to pump the cold water to spray arms 44A, 44B to pre-wash instruments 12. After a predetermined period of time, the pre-wash phase is terminated by deactivating motor 54. Controller 96 then opens valve 34 to allow the pre-wash fluid to drain from washing chamber 24. Once washing chamber 24 is drained, valve 34 is closed by controller 96.

Upon completion of the pre-wash phase, a washing phase is initiated. Controller 96 opens valve 66 in hot water line 62 to allow hot water from an external source (the institution's water system) to enter washing chamber 24. The hot water enters washing chamber 24 through diffuser 64 which directs the hot water against top wall 22a and side walls 22c of housing 22. The temperature of the hot water from the institution's water system may vary greatly in temperature. Nonetheless, introducing the hot water against the surface of housing 22 gradually heats the surfaces of housing 22, which are at a lower temperature as a result of the "cold water" pre-wash phase. When the sump is filled with sufficient amounts of the incoming hot water, controller 96 closes valve 66. Using signals from temperature sensor 92 in sump 26, controller 96 determines whether the water within sump 26 is at a desired temperature (typically about 150° F.) for the washing phase. (As will be appreciated, detergents or other washing chemicals are typically added to the hot water for the wash phase). If the temperature of the water is below a desired operating temperature, controller 96 energizes heating element 28 to bring the washing fluid within sump 26 to the desired washing temperature. Once at the desired washing temperature, controller 96 energizes motor 54, which in turn energizes pump 52 to pump the heated washing fluid to rotary spray arms 44A, 44B. Because the incoming hot water has warmed the inner surfaces of housing 22, and further has wetted spray arms 44A, 44B and instruments 12, the introduction of the heated washing fluid into washing chamber 24 does not produce as severe a thermal shock to washing chamber 24 as would have existed if hot water were introduced directly into sump 26, heated and then sprayed into washing chamber 24 that was previously chilled by the cold water pre-wash phase. In other words, by introducing hot water onto the surfaces within washing chamber 24, the temperature difference between the inner surfaces of washing chamber 24, as well as the air within washing chamber 24, is not as great as would exist if heated water were pumped directly into sump 26, heated and then sprayed into the previously chilled washing chamber 24. After a predetermined period of time, the wash phase is terminated by deactivating motor 54. Controller 96 then opens valve 34 to allow the wash fluid to drain from washing chamber 24. Once washing chamber 24 is drained, valve 34 is closed by controller 96.

Following the wash phase, a rinse phase is initiated. Controller 96 operates valve 66 to allow hot water from the facilities' hot water lines into washing chamber 24 through diffuser 64. As above, hot water entering washing chamber 24 is directed by diffuser 64 against top wall 22a and side walls 22c. A portion of the hot water also falls onto instruments 12. The hot water entering washing chamber 24 may have a temperature that is only slightly less than the temperature of the washing fluid used during the washing phase. In this respect, the likelihood of thermal shock occurring between the washing phase and the rinsing phase is relatively small. Nevertheless, the hot water introduced into washing chamber 24 through diffuser 64 helps reduce any temperature difference that may exist between surfaces within washing chamber 24 and the temperature of the water flowing through diffuser 64. Once sump 26 has been filled with the appropriate amount of hot water, controller 96 closes valve 66 and energizes motor 54 to cause pump 52 to circulate the rinse fluid through rotary spray arms 44A, 44B to rinse washing fluid from instruments 12. After a predetermined period of time, the rinse phase is terminated by deactivating motor 54. Controller 96 then opens valve 34 to allow the rinse fluid to drain from washing chamber 24. Once washing chamber 24 is drained, valve 34 is closed by controller 96.

Following the rinse phase, a thermal rinse phase is preferably performed. The thermal rinse phase is performed using high-quality, pure water from an external source. The pure water is introduced to washing chamber 24 through fluid inlet line 82. Controller 96 controls valve 86 to allow a pre-determined amount of pure water to enter washing chamber 24 through diffuser 84. Typically, the pure water would have a temperature at or below room temperature. Because the aforementioned rinse phase is performed using hot water from the facilities' water system, the temperature of the surfaces within washing chamber 24 would have a temperature near the temperature of the hot water used during the rinse phase. Introducing the pure water through diffuser 84 allows the pure water, having a temperature at room temperature or below, to stream onto the inner surfaces of upper wall 22a and side walls 22c thereby reducing the temperature of these surfaces. When a sufficient amount of pure water has filled sump 26, controller 96 causes valve 86 to close, and then causes heating element 24 to heat the pure water to a desired "thermal rinse temperature." Typically, a thermal rinse is conducted at between 180° F. and 194° F. Once the desired thermal rinse temperature has been attained, controller 96 energizes motor 54 that causes pump 52 to pump the heated rinse fluid to rotary spray arms 44A, 44B to rinse medical instruments 12. Following a pre-determined amount of time wherein the instruments are rinsed by the rinse fluid, controller 96 terminates the washing cycle and the rinse fluid is drained from chamber 24 through drain line 32, as described above.

During each of the foregoing phases of a washing cycle, when incoming water to diffusers 64, 74 and 84 is shut off, concave inner surface 122b of end wall 122 and aperture 144 that communicates therewith insures that all water within diffusers 64, 74 and 84 drains therefrom. As will also be appreciated, if a diffuser 64, 74 and 84 is mounted to a side wall 22c, such that axis "A" is oriented horizontally, the generally cylindrical shape of inner chamber 118 and apertures 142 will also insure that all water within diffusers 64, 74, 84 is drained therefrom.

Because the water entering washing chamber 24 through diffusers 64, 74, 84 is hot or cold (depending upon the phase of the washing cycle), the inner surfaces of washing chamber 24 as well as the components and articles therein are heated or cooled by the incoming water prior to initiation of an operating phase. The initial warming or cooling of surfaces in washing chamber 24 and the components therein helps prevent thermal shock that would normally occur in conventional washers when hot or cold fluid in sump 26 is introduced into the washing chamber through the spray arms at the start of a phase of a washing cycle. By initially distributing the fluid over the inner surfaces of washing chamber 24 as well as the components therein, walls 22a, 22c of washing chamber 24 can more gradually heat up or cool down and be less susceptible to rapid thermal expansion that can occur if hot or cold fluid is introduced suddenly into a cold or hot washing chamber 24. In addition, by introducing the washing fluid "F" into washing chamber 24 through diffusers 64, 74, 84, medical instruments 12 to be cleaned will be "wetted" prior to each phase of a washing cycle. This pre-wetting of the medical instruments allows any soil or debris thereon to soften and further facilitates enhanced cleaning of the medical instruments during the washing cycle.

The present invention thus provides a washing chamber and diffusers that allow water entering washing chamber 24 to contact surfaces of washing chamber 24 to effect a rapid heating or cooling of surfaces in washing chamber 24. The introduction of water as described herein will reduce thermal shock to the washing structure that may occur should water of a different temperature than the washing chamber be rapidly introduced into washing chamber 24 as a spray through sprayers 44A, 44B, which spray rapidly heats or cools the air within washing chamber 24. By warming or cooling washing chamber 24 during the introduction of the fluid into washing chamber 24, the need for a two-speed pump having a low speed is eliminated, and a single-speed pump may be used to introduce heated or cooled fluid into washing chamber 24 through diffusers 64, 74, 84. As a result, smaller, less expensive washers and disinfectors can be provided at a reduced cost.

The foregoing description is a specific embodiment of the present invention. It should be appreciated that this embodiment is described for purposes of illustration only, and that numerous alterations and modifications may be practiced by those skilled in the art without departing from the spirit and scope of the invention. For instance, as indicated above, diffusers 64, 74, 84 may be located on side walls 22c of washer 10 in addition to top wall 22a of washer 10 to facilitate more uniform distribution of the incoming water. Moreover, depending upon the location of diffusers 64, 74, 84 within washer 10, apertures 142 in domed portion 114 of diffusers 64, 74, 84 can be positioned and oriented so as to direct the fluid (water) to different parts of washer 10 to warm or cool the same. In other words, the angle of apertures 142 in a diffuser 64, 74, 84 may vary within the diffuser, and the position of apertures 142 in a diffuser 64, 74, 84 may also be varied to produce a stream or streams of fluid to a specific portion or portions of washing chamber 24. In this respect, diffusers 64, 74, 84 may have different aperture spacing and orientation for use in a washer/disinfector. It is intended that all such modifications and alterations be included insofar as they come within the scope of the invention as claimed or the equivalents thereof.

Having described the invention, the following is claimed:

1. A washing apparatus for washing medical devices, said washing apparatus having:

a washing chamber in which said medical devices are positioned for washing;

a plurality of fluid delivery assemblies comprising first and second fluid delivery assemblies configured to respectively provide first and second fluids to said washing chamber, said second fluid being provided to said washing chamber after said first fluid is provided to said washing chamber, said first and second fluid delivery assemblies respectively comprising:

first and second fluid diffusers mounted to a top wall of said washing chamber, each of said fluid diffusers comprising a tubular body portion having a domed portion at one end thereof, said domed portion having an inner chamber, said inner chamber communicating with an exterior of said domed portion through outer apertures extending through an outer cylindrical surface of said domed portion, said outer apertures of said first and second fluid diffusers being oriented toward said top wall and configured to respectively direct said first and second fluids toward said top wall; and first and second fluid inlet lines respectively connected to said first and second fluid diffusers and to first and second external fluid sources from which said first and second fluids are respectively and freshly provided to said first and second fluid diffusers, said first and second fluid inlet lines being configured to respectively provide said first and second fluid diffusers with said first and second fluids;

a sump located at a bottom of the washing chamber, the sump being configured to collect and hold said fluids provided to said washing chamber;

a heating element in said sump configured to heat said fluids held in said sump;

a sprayer configured to spray said fluids held in said sump on said medical devices to be cleaned; and a pump configured to pump said fluids held in said sump to said sprayer.

2. A washing apparatus as defined in claim 1, wherein said outer apertures are equi-spaced about an axis extending through said domed portion.

3. A washing apparatus as defined in claim 1 or 2, wherein said domed portion further includes an end wall and an end aperture extending through said end wall.

4. A washing apparatus as defined in claim 1, wherein each of said fluid diffusers is generally symmetrical about an axis, and wherein said domed portion further includes an end wall and an end aperture, said end wall being generally perpendicular to said axis, said end aperture extending through said end wall from a concave inner surface of said end wall to the exterior of said domed portion.

5. A washing apparatus as defined in claim 4, wherein said axis is in a vertical orientation, and wherein said end aperture is disposed at a lowermost part of said domed portion.

6. A washing apparatus as defined in claim 5, wherein said end aperture is aligned with said axis.

7. A washing apparatus as defined in claim 1, wherein said outer cylindrical surface of said domed portion has a diameter that is greater than a diameter of an outer cylindrical surface of said body portion.

8. A washing apparatus as defined in claim 1, wherein said domed portions respectively include annular slots configured to respectively mount said first and second fluid diffusers to said top wall.

9. A washing apparatus as defined in claim 1, wherein said tubular body portion defines a bore that communicates with said inner chamber in said domed portion, and wherein said outer apertures are each dimensioned such that a total cross-sectional area of all of said outer apertures extending through said outer cylindrical surface of said domed portion is equal to or less than a cross-sectional area of said bore.

10. A washing apparatus as defined in claim 1, wherein each of said fluid diffusers is symmetrical about an axis, wherein said domed portion further has an end wall generally perpendicular to said axis, and wherein said outer apertures are each directed away from said end wall.

11. A washing apparatus as defined in claim 10, wherein said outer apertures are each directed away from said end wall at an angle of about 10 degrees relative to a plane perpendicular to said axis.

12. A washing apparatus as defined as claim 1, wherein said outer apertures extend through a lateral side of said domed portion.

13. A washing apparatus as defined as claim 1, wherein said top wall is horizontal.

14. A washing apparatus as defined in claim 1, wherein said first fluid is a first one of a hot water fluid, a cold water fluid, and a high-quality pure water fluid, and wherein said second fluid is a second one of said hot water fluid, said cold water fluid, and said high-quality pure water fluid.

15. A washing apparatus as defined in claim 1, wherein said plurality of fluid delivery assemblies further comprises a third fluid delivery assembly configured to provide a third fluid to said washing chamber, said third fluid being provided to said washing chamber after said second fluid is provided to said washing chamber, wherein said third fluid delivery assembly comprises a third fluid diffuser mounted to said top wall of said washing chamber, said third fluid diffuser comprising a tubular body portion having a domed portion at one end thereof, said domed portion having an inner chamber, said inner chamber communicating with an exterior of said domed portion through outer apertures extending through an outer cylindrical surface of said domed portion, said outer apertures of said third diffuser being oriented toward said top wall and configured to direct said third fluid toward said top wall, wherein said third fluid delivery assembly further comprises a third fluid inlet line connected to said third fluid diffuser and a third second external fluid source from which said third fluid is freshly provided to said third fluid diffuser, said third fluid inlet line being configured to provide said third fluid diffuser with said third fluid.

16. A washing apparatus as defined in claim 15, wherein said first fluid is a first one of a hot water fluid, a cold water fluid, and a high-quality pure water fluid, wherein said second fluid is a second one of said hot water fluid, said cold water fluid, and said high-quality pure water fluid, and wherein said third fluid is a third one of said hot water fluid, said cold water fluid, and said high-quality pure water fluid.

17. A washing apparatus for washing medical devices, said washing apparatus having:

a washing chamber;

a sump at the bottom of the washing chamber configured to collect and hold fluids;

a heating element in said sump configured to heat fluids held in said sump;

a sprayer configured to spray said fluids held in said sump on said medical devices to be cleaned;

two or more fluid diffusers mounted to a wall defining said washing chamber, each of said fluid diffusers being configured to provide a respective one of said fluids to said sump via said washing chamber, each of said fluid diffusers comprising a tubular body portion having a domed portion at one end thereof, said domed portion having an inner chamber, said inner chamber communicating with an exterior of said domed portion through outer apertures extending through an outer cylindrical surface of said domed portion, each of said outer apertures extending through said outer cylindrical surface of said domed portion being directed toward said wall on which said fluid diffusers are mounted, each of said outer apertures being configured to direct said respective one of said fluids toward said wall on which said fluid diffusers are mounted;

a pump configured to pump fluids held in said sump to said sprayer; and two or more fluid inlet lines, each of said fluid inlet lines being connected to a respective one of the fluid diffusers, each of said fluid inlet lines being configured to provide said respective one of said fluids freshly from a corresponding external source to said respective one of said fluid diffusers.

* * * * *